(12) United States Patent
McCoy et al.

(10) Patent No.: US 7,859,273 B2
(45) Date of Patent: Dec. 28, 2010

(54) SENSOR FOR DETECTING ORGANIC LIQUIDS

(75) Inventors: Kenneth McCoy, Redwood City, CA (US); Robert Wasley, San Carlos, CA (US); Peter Wijeratne, San Carlos, CA (US); Paul Hauptly, Bluffton, SC (US)

(73) Assignee: Tyco Thermal Controls LLC, Menlo Park, CA (US)

( * ) Notice: Subject to any disclaimer, the term of this patent is extended or adjusted under 35 U.S.C. 154(b) by 344 days.

(21) Appl. No.: 12/095,590

(22) PCT Filed: Dec. 1, 2006

(86) PCT No.: PCT/US2006/061531

§ 371 (c)(1),
(2), (4) Date: May 30, 2008

(87) PCT Pub. No.: WO2007/065163

PCT Pub. Date: Jun. 7, 2007

(65) Prior Publication Data

US 2010/0219849 A1    Sep. 2, 2010

Related U.S. Application Data

(60) Provisional application No. 60/741,838, filed on Dec. 3, 2005.

(51) Int. Cl.
*G01R 27/22* (2006.01)

(52) U.S. Cl. ............... 324/693; 324/453; 422/68.1; 422/82.02; 73/40.5 R; 73/304 R

(58) Field of Classification Search ............ 324/693, 324/453; 422/68.1, 82.01; 73/40.5 R, 304 R
See application file for complete search history.

(56) References Cited

U.S. PATENT DOCUMENTS

| 4,855,706 A | 8/1989 | Hauptly | |
|---|---|---|---|
| 5,148,708 A | 9/1992 | Murata et al. | |
| 5,378,995 A * | 1/1995 | Kudo et al. | 324/693 |

FOREIGN PATENT DOCUMENTS

EP    0306182 A2    3/1989

\* cited by examiner

*Primary Examiner*—Vincent Q Nguyen

(57) ABSTRACT

A sensor for detecting the presence of an organic liquid. The sensor includes an a elongate substrate having a first and second opposed surface, and a first sensor surface disposed on at least a portion of the first surface of the substrate and a second sensor surface disposed on at least a portion of the second surface of the substrate. The sensor also includes a bridging electrode electrically coupling the first and second sensor surfaces, a first electrode disposed on the first surface of the substrate and electrically coupled to the first sensor surface, and a second electrode disposed the second surface of the substrate and electrically coupled to the second sensor surface.

20 Claims, 6 Drawing Sheets

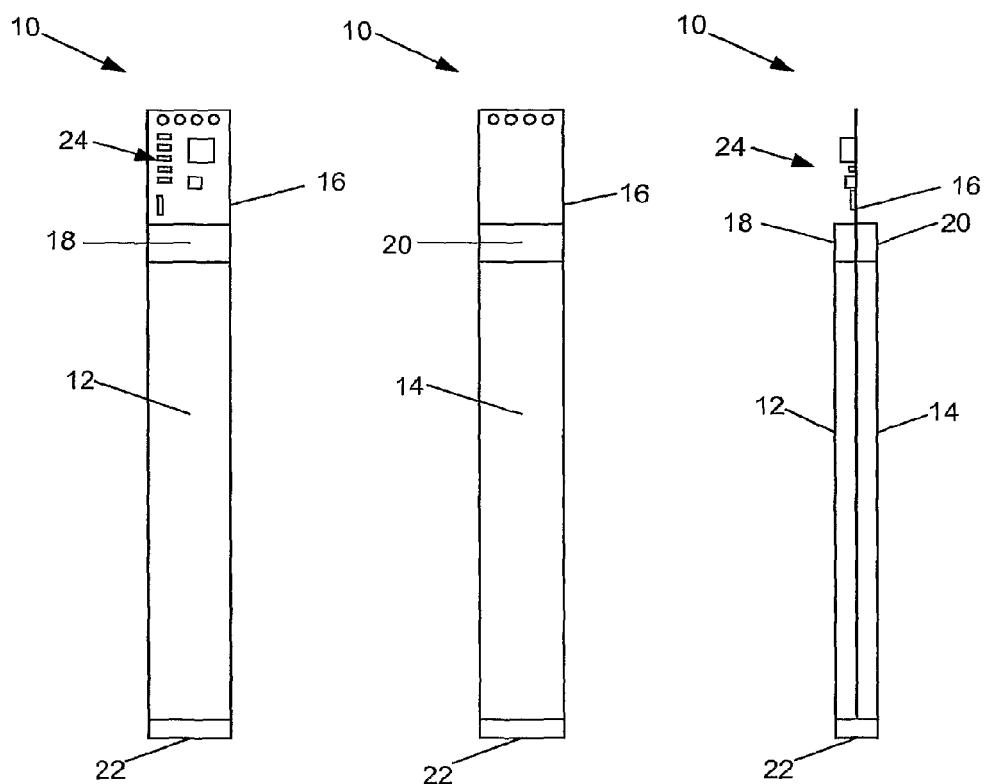

SENSOR FOR DETECTING ORGANIC LIQUIDS

CROSS-REFERENCE TO RELATED APPLICATIONS

This application claims the benefit of U.S. provisional patent application Ser. No. 60/741,838, filed Dec. 3, 2005, the entire disclosure of which is incorporated herein by reference.

FIELD

The present invention generally pertains to sensors for detecting the presence of organic liquids.

BACKGROUND

Certain organic liquids, such as hydrocarbon fuels, may present personal and environmental hazards when present outside of their associated containers. For example, due to the significant volume of liquid that may be contained in above-ground and underground fuel storage tanks, an undetected leak in a storage tank may result in a great deal of contamination. Detecting leakage of such liquids into undesired areas can be important in the control and/or avoidance such contamination.

BRIEF DESCRIPTION OF THE DRAWINGS

Features and advantages of the present invention are set forth by the description of various embodiments consistent therewith, which description should be considered in combination with the accompanying drawings, wherein:

FIG. 1 is a front view of an embodiment of a sensor consistent with the present disclosure;

FIG. 2 is a rear view of the sensor embodiment shown in FIG. 1;

FIG. 3 is a side view of the sensor embodiment shown in FIG. 1;

DESCRIPTION

Figure 4:
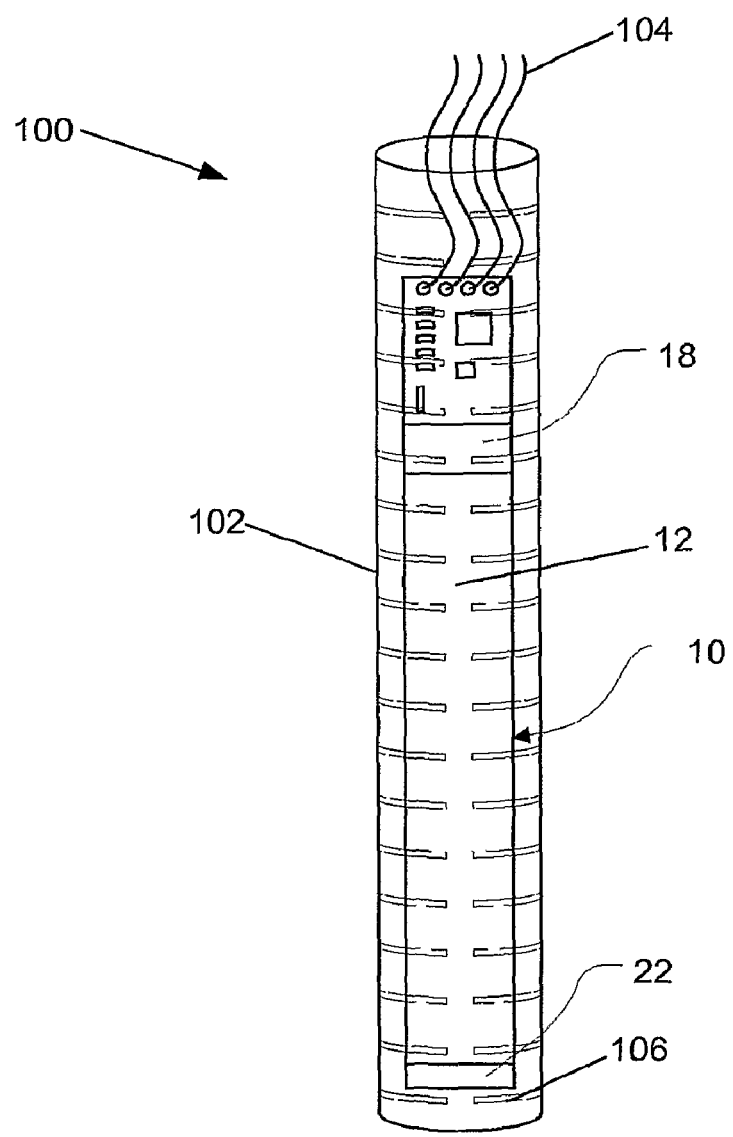
FIG. 4 shows an embodiment of a sensor assembly consistent with the present disclosure.

A sensor according to the present disclosure may detect the presence of an organic liquid. Generally, the sensor may exhibit a first state in the absence of an organic liquid and may exhibit a second state when an organic liquid is in contact with a sensor surface. The first and second state of the sensor may generally be related to a change in the resistance between a first and second electrode when a sensor surface is in contact with an organic liquid. The sensor may present a generally elongate sensor surface, and may detect contact between an organic liquid and the sensor surface at any point along the elongate senor surface. Accordingly, in one exemplary embodiment, a sensor consistent with the present disclosure may be suitably employed for detecting the presence of an organic liquid in a sump, manhole, etc. in which the organic liquid may be present at an indeterminate height within the sump or manhole.

Referring to FIGS. 1-3, an embodiment of a sensor 10 may generally include a first and second sensor surface 12, 14 disposed on opposed sides of an electrically non-conductive substrate 16. The sensor surfaces may be formed from a variable resistance material. First and second electrodes 18, 20 may each be coupled to a respective one of the sensor surfaces 12, 14 on respective sides of the substrate 16. A bridging electrode 22 may be electrically coupled to both of the sensor surfaces 12, 14. The electrodes 18, 20, 22 may be formed from any suitable electrically conductive material, e.g., copper, gold, platinum, silver, etc. In the illustrated exemplary embodiment, the first and second electrodes 18, 20 are positioned adjacent a first end of the substrate 16 and the bridging electrode 22 is positioned adjacent a second end of the substrate 16. Various other configurations may also be employed, however.

The substrate 16 may support the sensor surfaces 12, 14 and electrodes 18, 20, 22, and may electrically insulate the respective sensor surfaces 12, 14 and the electrodes 18, 20 from one another. Accordingly, an electrical pathway may exist between the first and second electrodes 18, 20 through the respective sensor surfaces 12, 14 and the bridging electrode 22, which electrically couples the first and second sensor surfaces 12, 14.

The variable resistance material of the sensor surfaces 12, 14 may be responsive to contact with organic liquids. The conductive pathway through the sensor surfaces 12, 14 and the bridging electrode 22 may have a first resistance when the sensor surfaces 12, 14 are in contact with an organic liquid, and may have a second resistance in the absence of an organic liquid. Accordingly, the presence or absence of an organic liquid in contact with the sensor surfaces 12, 14 may be determined based on the resistance measured between the first and second electrodes 18, 20.

Variable resistance materials may generally include a mixture of a swellable matrix material and conductive filler, as described for example in U.S. Pat. No. 4,855,706 to Hauptly, the entire disclosure of which is incorporated herein by reference. The matrix material may be reversibly swellable in the presence of an organic liquid. That is, when the swellable matrix material is in contact with an organic liquid, the matrix material may swell. The concentration of the conductive filler may be provided to produce a first resistance when the matrix material is in an un-swelled condition, i.e., in the absence of an organic liquid. In the presence of an organic liquid, the matrix material may swell, thereby increasing the average distance between the particles of the conductive filler. The increase in the distance between the particle of the conductive filler may result in a second, higher, resistance when the variable resistance material is in contact with an organic liquid.

Suitable variable resistance materials are known to those having skill in the art. One embodiment of a variable resistance material may include a mixture of silicone and graphite. The silicone may be swellable when it is in contact with an organic liquid. The swelling of the silicone may be reversible, such that the silicone may return to an unswelled condition when it is removed from contact with the organic liquid. The graphite filler may provide electrical conductivity through the variable resistance material. Various other swellable matrices and conductive fillers may be employed. For example, the swellable matrix may be selected to provide increased sensitivity to a particular organic liquid, or family of organic liquids. The conductive filler may be selected, e.g., to resist environmental conditions or chemical attack based on specific applications, in addition to providing electrical conductivity. Numerous other factors may be considered for selecting the matrix and filler material for the variable resistance material.

In one embodiment, the sensor 10 may be constructed using a known double-sided printed circuit board, e.g., including a conductive plating on each opposed sides of a fiberglass substrate. The sensor substrate 16 may be provided by a fiberglass circuit board substrate. The copper plating of the printed circuit board may be etched to provide a bare region on each side of the circuit board for the sensor surfaces 12, 14, and to leave conductive traces for the first and second electrodes 18, 20 adjacent to one end of the circuit board. Similarly, the bridging electrode 22 may be formed by leaving a conductive trace on each side of the circuit board adjacent to a second end of the circuit board. The conductive traces adjacent to the second end of the circuit board may be electrically coupled, e.g., via plated through holes, jumpers, etc.

The sensor surfaces 12, 14 may be provided by coating the bare regions of the circuit board between the respective electrodes 18, 20 and a portion of the bridging electrode 22 with a variable resistance material. For example, a variable resistance material composition of graphite and silicone may be applied to the fiberglass substrate of the circuit board by spraying, e.g., air or airless spraying, brushing, dipping, screen printing, etc. The components of the variable resistance material may be thoroughly mixed such that the graphite component is generally uniformly dispersed in the silicone matrix. The variable resistance material may be electrically coupled to the electrodes 18, 20, and 22, e.g., by at least partially overlying or contacting the electrodes 18, 20, 22.

As shown, circuitry 24 for monitoring the resistance across the first and second electrodes 18, 20 may be disposed on the substrate 16. The resistance across the first and second electrodes 18, 20 may be indicative of the resistance of the variable resistance material making up the senor areas 12, 14, which may in turn indicate contact, or lack of contact, with an organic liquid. In an embodiment in which the sensor 10 is formed on a printed circuit board, the wiring pathways for the circuitry may be etched from the conductive layer of the printed circuit board, and the components of the circuitry 24 may be mounted to the circuit board in the conventional manner of a printed circuit. The circuitry 24 may be protected, e.g., by encapsulation in epoxy, etc., or by a protective housing, etc.

In one embodiment, the circuitry 24 may convert a detected analog resistance of the conductive pathway through the sensor surfaces 12, 14, etc. to a binary output. That is, the circuitry 24 may provide a first output when a first resistance, corresponding to no contact with an organic liquid, is detected. The circuitry 24 may, correspondingly, provide a second output when a second resistance, corresponding to contact with an organic liquid, is detected. In this manner, the output of the circuitry 24 may indicate whether an organic liquid is in contact with the sensor surfaces 12, 14.

In one embodiment, the circuitry 24 may include a comparator circuit that is compatible with commercially available monitoring devices and systems. For example, the circuitry 24 may include a comparator circuit that is compatible with the available voltage and current delivered by TraceTek brand instruments, manufactured by Tyco Thermal Controls of Menlo Park, Calif., which is typically used for sensor cable monitoring circuits.

In some embodiments the sensor may be compatible with low power leak monitoring circuits which may measure the resistance along the circuit to determine the physical location of the sensor circuit. Low power monitoring circuits used in the TracTek Brand instruments are well known, and described, for example, in U.S. Pat. No. 5,235,286 to Masia et al, the entire disclosure of which is incorporated herein by reference. In a system including multiple sensors 10, a low power leak monitoring circuit may configured to determine which of the multiple sensors 10 has come in contact with an organic liquid.

Referring also to FIG. 4, a sensor assembly 100 consistent with the present disclosure may include a sensor 10 and a protective housing 102. The sensor 10 may be coupled to a control system via leads 104. The protective housing 102 may provide at least some degree of protection against mechanical damage to the sensor 10. For example, the sensor surfaces 12, 14 may be susceptible to abrasion damage, etc. The protective housing may include mounting features for locating the sensor within the protective housing. The mounting features may, in some embodiments maintain the sensor generally centered within the housing, although other configurations may alternatively be employed.

According to one embodiment, the protective housing 102 may include a tube or tube, and may include at least one opening 106. A liquid surrounding the protective housing 102 may enter through openings 106 and may contact the sensor 10, allowing sensor to determine the presence of an organic liquid. The size and number of the openings may be selected to accommodate the viscosity of the organic liquid. For example, in an application for detecting the presence of a relatively viscous organic liquid, e.g., a heavy oil, the openings 106 may be relatively large to allow the level of the liquid within the protective housing 102 to change rapidly in response to changes in the level of the liquid surrounding the sensor assembly 102. In an application for detecting a lower viscosity liquid, smaller openings 106 may be used while still achieving the rapid changes in liquid height within the protective housing. In various embodiments the openings may range from, for example, 4 mm-7 mm, although other opening sizes may be employed.

The protective housing 102 may be formed from a variety of materials and configurations. For example, a cost effective protective housing may be formed from a polyvinylchloride (PVC) tube including one, or a plurality, of openings, e.g., longitudinal or circumferential slots, allowing liquid communication between the interior and exterior of the tube. The sensor 10 may be disposed within the PVC tube. In an application associated with the detection of explosive or flammable liquids, e.g., gasoline, fuel oil, etc., the protective housing may be configured to reduce the risk of a static discharge, which may ignite the liquid or vapor. For example, the protective housing may be a tube including an anti-static additive, a variety of which are known to those having skill in the art. In one embodiment, the tube forming the protective housing may include a polypropylene tube including an anti-static additive. Various other tube materials and configurations may also suitably be used in connection with a sensor assembly consistent with the present disclosure.

As shown, the sensor 10 may be provided having a generally elongate configuration, which may include an elongate substrate 16 and may provide an elongate sensor surface 12, 14 between the electrodes 18, 20 and the bridging electrode 22. An organic liquid contacting one or both of the sensor surfaces 12, 14 may increase the resistance of the portion of the variable resistance material making up the sensor surface 12, 14 that is contacted by the organic liquid. Because the sensor surfaces 12, 14 in combination with the bridging electrode 22 provide a continuous electrical pathway between the first and second electrodes 18, 20, an increase in the resistance of any portion of the variable resistance material making up the sensor surfaces 12, 14 may be detected as an increase in the resistance between the first and second electrodes 18, 20. The sensor 10 may, therefore, indicate contact with an organic liquid, e.g., through an increase in the resistance between the first and second electrodes 18, 20, regardless of the position of the organic liquid along the length of the sensor surface 12, 14.

The ability of the sensor 10 to indicate contact with an organic liquid at any point along the length of the sensor surfaces 12, 14 may be advantageous for various applications in which the organic liquid may occur at an indeterminate location. For example, many organic liquids, such as hydrocarbon oils or fuels, may generally float on water. In an application in which the level of the water, upon which the organic liquid is floating, may vary, the location, or height, at which the organic liquid is present may vary according to the level of the water.

Referring also to FIGS. 5 through 8, in one application the sensor may be disposed in a sump 107 for monitoring the presence of organic liquids. For the purpose of clarity, only the sensor 10 is shown. However, it will be appreciated that a sensor assembly including a protective housing, as shown in FIG. 4, may be employed. In the illustrated embodiment, the sump 107 may contain varying depths of water. Depending upon the height of the water level relative to the sensor, the portion of the sensor surfaces 12, 14 that may be in contact with an organic liquid floating on the water may vary. Of course, the same concept is equally applicable to organic liquids other than hydrocarbon oils or fuels. The length of the sensor 10 may be selected to correspond with anticipated liquid level heights within the sump.

Figure 5:
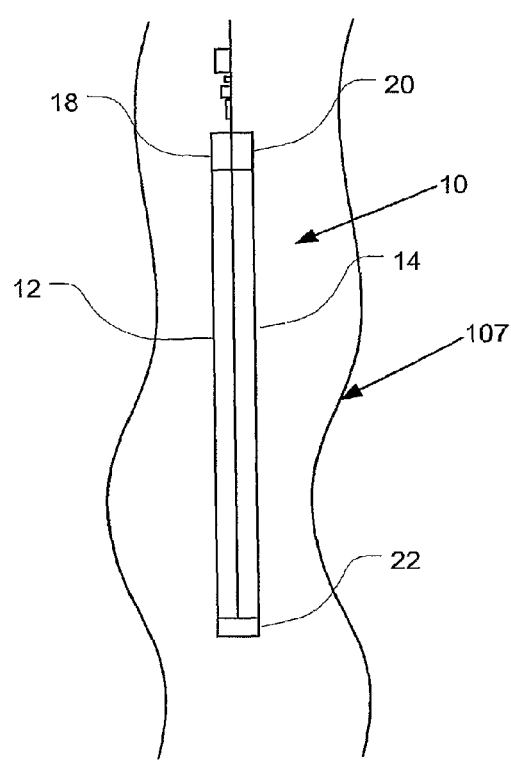
FIG. 5 depicts a sensor consistent with the present disclosure positioned for detecting the presence of an organic liquid in a sump.
Figure 6:
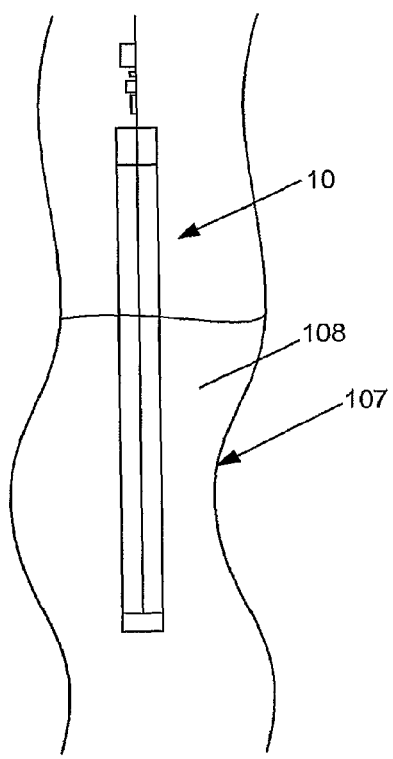
FIG. 6 depicts the sensor arrangement of FIG. 5 in the presence of water.

As shown in FIG. 5, when the sump 107 is free of both water and any organic liquids, e.g., a dry condition, the sensor 10 may exhibit a first state corresponding to a relatively low resistance across the electrodes 18, 20. In an embodiment utilizing a TraceTek control system, the first state may be a high resistance output across the TraceTek circuit indicating that organic liquids are not present. The high resistance output across the TraceTek circuit may be provided by the circuitry of the sensor 10 in response to the low resistance state of the sensor surfaces. Similarly, when the sump 107 contains water 108 contacting the sensor 10, as shown in FIG. 6, but does not include an organic liquid, the sensor 10 may also exhibit a first state corresponding to a relatively low resistance across the electrodes 18, 20. The circuitry of the sensor 10 may provide a sensor output according to the requirements of a detection system to indicate the absence of an organic liquid.

Figure 7:
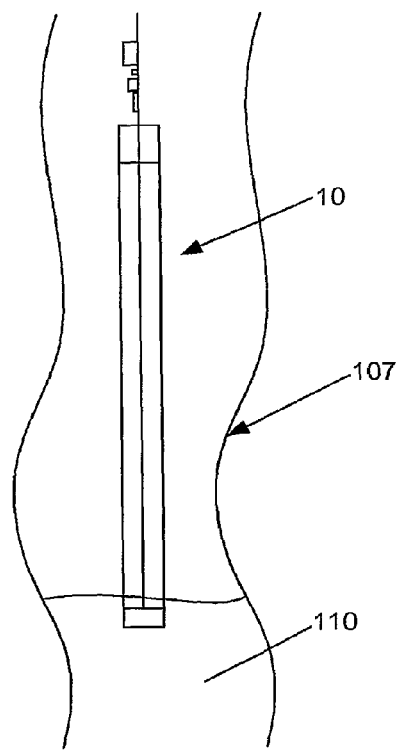
FIG. 7 depicts the sensor arrangement of FIG. 5 in a sump containing fuel.

Turning to FIG. 7, when an organic liquid 110, such as fuel is present in the sump 107 at a liquid level height sufficient to contact at least a portion of the sensor surfaces, the portion of the variable resistance material of the sensor surfaces contacted by the organic liquid 110 may have a relatively high resistance. Since the electrical path between the first and second electrodes of the sensor 10 includes the entire longitudinal expanse of the sensor surfaces, an increase in the resistance of the portion of the variable resistance material of the sensor surfaces contacted by the organic liquid results in an increase in the resistance between the first and second electrodes. In response to the increased resistance, the sensor 10 may exhibit a second state indicating the presence of an organic liquid. The relatively high resistance of the conductive pathway may be conditioned by the sensor circuitry to provide a second sensor output or second sensor state according to the requirements of a detection system to indicate the presence of an organic liquid 110.

Figure 8:
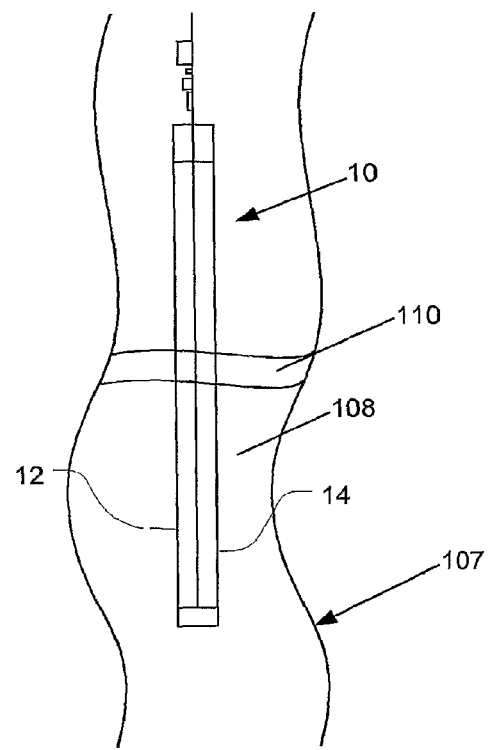
FIG. 8 depicts the sensor arrangement of FIG. 5 in a sump containing water and fuel.
Figure 9:
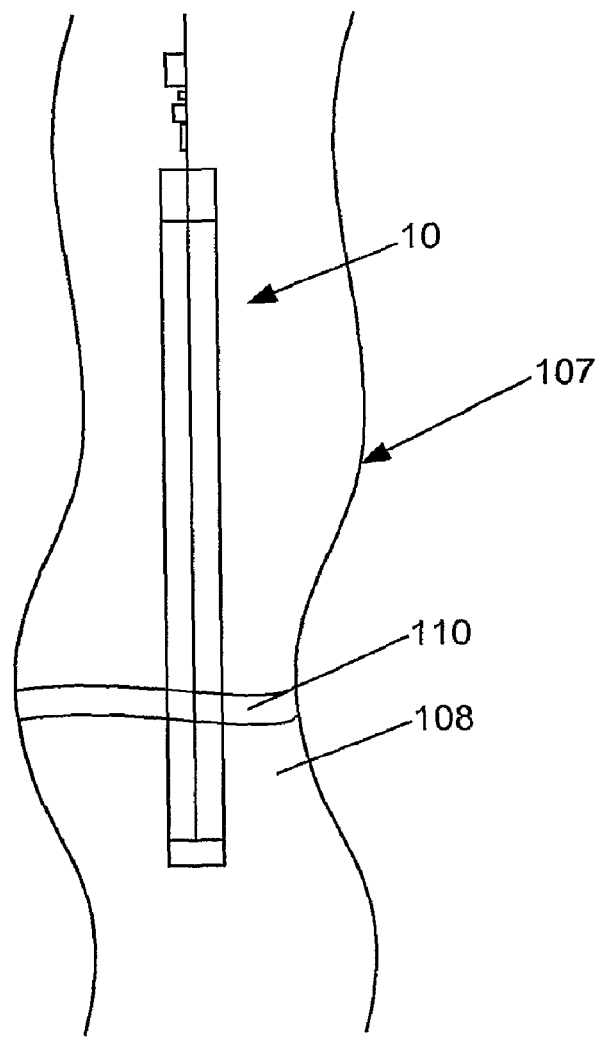
FIG. 9 depicts the sensor arrangement of FIG. 5 in a sump containing water and fuel.

As shown in FIGS. 8 and 9, an organic liquid 110 may float on top of water 108 or other liquid present in the sump 107. While the resistance of the regions of the sensor surfaces contacted by the water 108 may be generally unchanged, the organic liquid 110 may swell the matrix of the sensor surfaces in the region of the variable resistance material of the sensor surfaces contacted by the organic liquid 110, increasing the resistance of the variable resistance material of the sensor surfaces in the contacted regions. The increased resistance in the regions contacted by the organic liquid 110 may increase the resistance between the first and second electrodes, and may cause the sensor to exhibit the second state indicating the presence of an organic liquid to a detection system.

As mentioned, the organic liquid 110 may float on the water 108. Therefore, even for the same amount of organic liquid 110, the height along the sensor 10 contacted by the organic liquid 110 may vary depending on the level of the water 108 in the sump, as shown in FIGS. 8 and 9. Consistent with the present disclosure, providing the first and second electrodes adjacent to a first end of the elongate substrate and providing elongate sensor surfaces extending between the first and second electrodes and a bridging electrode adjacent to a second end of the substrate, the electrical pathway may include the length of both of the sensor surfaces. The resistance between the first and second electrodes may be increased by contact with an organic liquid regardless of the position along the length of the sensor surfaces at which the organic liquid contacts the sensor surfaces. The sensor of the present disclosure may, therefore, allow the presence of an organic liquid to be detected even when contact between the sensor and the organic liquid may occur at an indeterminate position along the length of the sensor.

Figure 10:
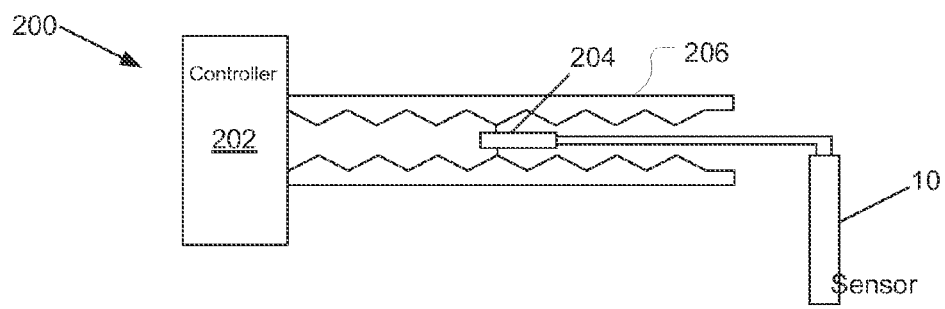
FIG. 10 illustrates one embodiment of detection system including a sensor consistent with the present disclosure.
Figure 11:
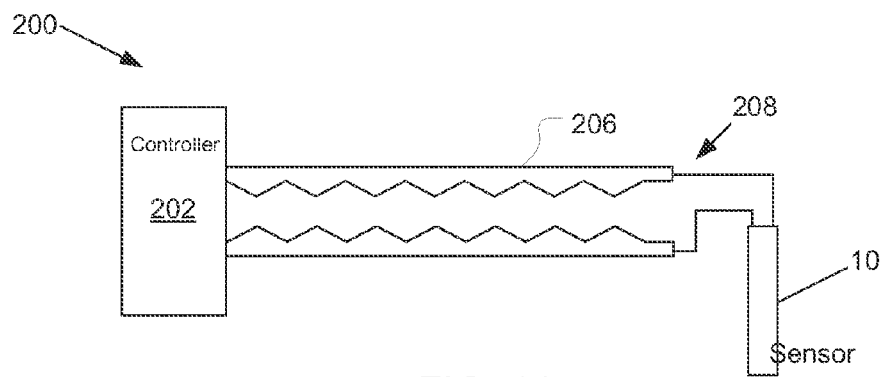
FIG. 11 illustrates a second embodiment of detection system including a sensor consistent with the present disclosure.

Referring to FIG. 10, a sensor 10 may be incorporated into a monitoring system 200. In one embodiment, the monitoring system 200 may include a system controller 202 and a system sensor circuit 206. In one embodiment the controller 202 may include any of several TraceTek brand instruments manufactured by Tyco Thermal Controls LLC, and the sensor circuit may be a sensor circuit corresponding to the selected TracTek brand instrument. The system 200 may also include various other sensor cable and interconnect components. As shown in FIG. 10, the sensor 10 may be coupled to the system 200 using a branch connector 204 or zone connector. Alternatively, as shown in FIG. 11, the sensor 10 may be integrated into the system 200 using a standard end circuit termination, generally indicated by 208.

Figure 12:
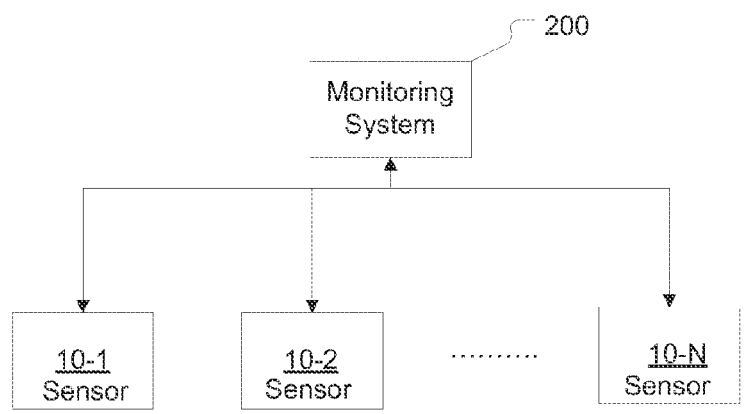
FIG. 12 illustrates one embodiment of a detection system including a plurality of sensors consistent with the present disclosure.

FIG. 12 illustrates a system consistent with one embodiment including a monitoring system 200, e.g. including a TraceTek brand controller and associated sensor circuit, coupled to a plurality of organic liquid sensors 10-1, 10-2 . . . 10-N consistent with the present disclosure. The monitoring system 200 may deliver an excitation current to each sensor 10-1, 10-2 . . . 10-N. For example, a TraceTek brand system may provide an excitation signal to the sensors including a DC or pulsed DC current of about 500 micro amps, or less, and at about 10 VDC, or less. The circuitry of the sensor may use at least a portion of the provided excitation signal to monitor the integrity of the TraceTek circuit. When a sensor is not in contact with an organic liquid, the sensor may not develop a substantial load on the TraceTek circuit. When the sensor is in contact with an organic liquid, the circuitry of the sensor may close a solid state switch across the TraceTek circuit. The TraceTek controller may interpret the closure of the switch as an indication of detected organic liquid. The controller may measure the resistance along the circuit to the sensor 10-1, 10-2 . . . 10-N determine the location of the sensor that has detected the organic liquid and provide an output indicative of the location. Accordingly, in a system including a plurality of organic liquid sensors, it may be possible to determine which of the sensors has detected the presence of an organic liquid.

While foregoing exemplary embodiments have included the use of TraceTek brand commercially available leak detection systems, other commercially available sensor control systems, as well as purpose-built systems, may be used in connection with a sensor herein. Additionally, as sensor herein may be configured for standalone use. For example, a sensor may include an integrated alarm or indicator to indicate the detection of an organic liquid. Various other configurations and embodiments will also be understood by those having skill in the art.

According to an aspect, the present disclosure may provide a system for detecting the presence of an organic liquid. The system may include an elongate substrate having first and second opposed surfaces. A first sensor surface may be provided on at least a portion of the first surface of the substrate and a second sensor surface may be provided on at least a portion of the second surface of the substrate. A bridging electrode may electrically couple the first and second sensor surfaces. A first electrode may be disposed on the first surface of the substrate and be electrically coupled to the first sensor surface, and a second electrode may be disposed the second surface of the substrate and be electrically coupled to the second sensor surface. The first and second sensor surfaces and the bridging electrode provide a conductive path between the first and second electrodes. The conductive path has a first resistance when at least one of the sensor surfaces is in contact with an organic liquid and a second resistance when the sensor surfaces are not in contact with an organic liquid. The system may also include a monitoring system configured to provide a first output in response to the first resistance and a second output in response to the second resistance.

According to another aspect, the present disclosure may provide a method of detecting an organic liquid. The method may include providing an elongate substrate having first and second opposed surfaces. The method may also include providing a first and second elongate sensor surface, each sensor surface disposed on a respective one of the opposed sides of the substrate. A bridging electrode may be provided electrically coupling the first at second sensor surfaces. The method may further include providing a first electrode on the first surface of the substrate and electrically coupled to the first sensor surface, and a second electrode disposed on the second surface of the substrate and electrically coupled to the second sensor surface, the first and second sensor surfaces and the bridging electrode providing a conductive pathway between the first and second electrodes, the conductive pathway having a first resistance when at least one of the sensor surfaces is in contact with an organic liquid and having a second resistance when the sensor surfaces are not in contact with an organic liquid. The method may also include providing an output based on a resistance between the first and second electrodes.

The embodiments described herein have been presented for the purpose of illustration, and are susceptible to numerous modifications and variations without materially departing from the inventive aspects thereof. Accordingly, the present invention should not be limited to the described embodiments, but should be afforded the full scope of the claims appended hereto.

What is claimed is:

1. A system comprising:
an elongate non-conductive substrate having first and second opposed surfaces;
a first sensor surface disposed on at least a portion of said first surface of said substrate and a second sensor surface disposed on at least a portion of said second surface of said substrate;
a bridging electrode electrically coupling said first and second sensor surfaces; and
a first electrode disposed on said first surface of said substrate and electrically coupled to said first sensor surface, and a second electrode disposed said second surface of said substrate and electrically coupled to said second sensor surface,
said first and second sensor surfaces and said bridging electrode providing a conductive path between said first and second electrodes, said conductive path having a first resistance when at least one of said sensor surfaces is in contact with an organic liquid and a second resistance when said sensor surfaces are not in contact with an organic liquid.

2. The system according to claim 1, said sensor further comprising circuitry configured to provide a first sensor state when said conductive pathway has said first resistance and a configured to provide a second sensor state when said conductive pathway has said second resistance.

3. The system according to claim 1, said circuitry being at least partially disposed on said substrate.

4. The system according to claim 1, wherein said first and second sensor surfaces comprise a variable resistance material comprising a swellable matrix and conductive filler.

5. The system according to claim 1, wherein said first and second sensor surfaces comprise a variable resistance material comprising a mixture of silicone and graphite.

6. The system according to claim 1, further comprising a protective housing disposed around at least a portion of said first and second sensor surfaces, said protective housing comprising at least one opening providing liquid communication between at least one of said first and second sensor surfaces and an exterior of said housing.

7. The system according to claim 6, wherein said protective housing comprises a tube, said substrate being at least partially disposed in said tube.

8. A system comprising:
at least one sensor comprising:
an elongate non-conductive substrate having first and second opposed surfaces,
a first sensor surface disposed on at least a portion of said first surface of said substrate and a second sensor surface disposed on at least a portion of said second surface of said substrate,
a bridging electrode electrically coupling said first and second sensor surfaces, and
a first electrode disposed on said first surface of said substrate and electrically coupled to said first sensor surface, and a second electrode disposed said second surface of said substrate and electrically coupled to said second sensor surface, said first and second sensor surfaces and said bridging electrode providing a conductive path between said first and second electrodes, said conductive path having a first resistance when at least one of said sensor surfaces is in contact with an organic liquid and a second resistance when said sensor surfaces are not in contact with an organic liquid; and a monitoring system coupled to said at least one sensor, said monitoring system being configured to provide a first output in response to said first resistance and a second output in response to said second resistance.

9. The system according to claim 8, said system comprising a plurality of said sensors coupled to said monitoring system.

10. The system according to claim 9, said monitoring system being configured to provide an output indicative of a location one of said plurality of sensors in contact with an organic liquid.

11. The system according to claim 8, said sensor further comprising circuitry configured to provide a first sensor state when said conductive pathway has said first resistance and a configured to provide a second sensor state when said conductive pathway has said second resistance.

12. The system according to claim 8, said circuitry being at least partially disposed on said substrate.

13. The system according to claim 8, wherein said first and second sensor surfaces comprise a variable resistance material comprising a swellable matrix and conductive filler.

14. The system according to claim 8, wherein said first and second sensor surfaces comprise a variable resistance material comprising a mixture of silicone and graphite.

15. The system according to claim 8, said system comprising a protective housing disposed around at least a portion of said first and second sensor surfaces, said protective housing comprising at least one opening providing liquid communication between at least one of said first and second sensor surfaces and an exterior of said housing.

16. The system according to claim 15, wherein said protective housing comprises a tube, said substrate being at least partially disposed in said tube.

17. A method of detecting an organic liquid comprising:

providing an elongate substrate comprising a first and second opposed surface;

providing a first and second elongate sensor surface, each sensor surface disposed on a respective one of said opposed sides of said substrate;

providing a bridging electrode electrically coupling said first at second sensor surfaces;

providing a first electrode on said first surface of said substrate and electrically coupled to said first sensor surface, and a second electrode disposed on said second surface of said substrate and electrically coupled to said second sensor surface, said first and second sensor surfaces and said bridging electrode providing a conductive pathway between said first and second electrodes, said conductive pathway having a first resistance when at least one of said sensor surfaces is in contact with an organic liquid and having a second resistance when said sensor surfaces are not in contact with an organic liquid;

allowing said organic liquid to contact said first and second sensor surfaces; and providing an output indicating presence of said organic liquid in response to said first resistance.

18. The method according to claim 17, further comprising positioning said first and second sensor surfaces in a protective housing and providing liquid communication between at least one of said sensor surfaces and an exterior of said housing.

19. The method according to claim 17 wherein said first and second sensor surfaces comprise a variable resistance material comprising a swellable matrix and a conductive filler.

20. The method according to claim 17, wherein said first and second sensor surfaces comprise a variable resistance material comprising a mixture of silicone and graphite.

* * * * *